United States Patent [19]

Wood et al.

[11] 4,093,745

[45] June 6, 1978

[54] METHOD FOR PRODUCING A PRILLED UREA BATH BEAD COMPOSITION

[75] Inventors: Donald C. Wood, Des Plaines; Robert L. McLaughlin, Wilmette, both of Ill.

[73] Assignee: DeSoto, Inc., Des Plaines, Ill.

[21] Appl. No.: 699,982

[22] Filed: June 25, 1976

Related U.S. Application Data

[63] Continuation-in-part of Ser. No. 635,282, Nov. 26, 1975.

[51] Int. Cl.² ............................................. A61K 7/50
[52] U.S. Cl. .................................... 424/358; 424/69; 424/359; 424/361; 424/363; 424/365
[58] Field of Search ................ 264/7, 13, 14; 424/69, 424/358, 359, 361, 363, 365

[56] References Cited

U.S. PATENT DOCUMENTS

| | | | |
|---|---|---|---|
| 1,734,260 | 11/1929 | Lamont | 264/14 |
| 3,196,079 | 7/1965 | Blaustein | 424/69 |
| 3,268,631 | 8/1966 | Price | 264/14 |
| 3,686,373 | 8/1972 | Griesheimer | 264/14 |
| 3,689,678 | 9/1972 | Fox | 424/365 |
| 3,851,065 | 11/1974 | Ludwig | 424/346 |
| 3,952,078 | 4/1976 | Bradley | 264/13 |

Primary Examiner—Albert T. Meyers
Assistant Examiner—A. P. Fagelson
Attorney, Agent, or Firm—Dressler, Goldsmith, Clement, Gordon & Shore, Ltd.

[57] ABSTRACT

A non-segregating, free-flowing bath bead composition, based on prilled urea in combination with active bath components, is produced by admixing urea prills with an oily liquid emollient to distribute the emollient substantially uniformly on the prills and then adhering a powdered surfactant to the emollient-bearing prills to produce free-flowing bath beads. If desired, color can be imparted to the prills by providing moisture-containing prills and commingling the prills with a powdered, water-soluble dye prior to the distribution of the emollient thereon.

15 Claims, No Drawings

METHOD FOR PRODUCING A PRILLED UREA BATH BEAD COMPOSITION

CROSS-REFERENCE TO RELATED APPLICATION

This application is a continuation-in-part of our copending application U.S. Ser. No. 635,282, filed on Nov. 26, 1975.

BACKGROUND OF THE INVENTION

The present invention relates to a method for producing bath bead compositions which utilize urea prills or beads which possess skin soothing characteristics as carriers for an oil liquid emollient and other active bath components.

At the present time, bath compositions are commercially available in the form of powders having a particle size ranging from fine powders to coarse granules. Such powders are usually constituted by an alkaline detergent material, such as anhydrous sodium tripolyphosphate, combined with small amounts of oils, perfumes, and dyes, to provide attractive coloration. Such products are occasionally irritating to portions of the human body due to the alkalinity that is imported to the bath water upon use.

In our above-identified copending application is disclosed an attractive bath bead composition which is useful at approximately neutral pH and which provides good emolliency without irritation to the skin or mucous membranes. The composition is of very low toxicity if ingested and, since it is in the form of beads instead of a powder, the composition presents a more pleasing and appropriate appearance in view of the fact that bath compositions are usually sold under the designation "bath beads." Moreover, a composition in bead form minimizes undesirable dusting during manufacture and dispensing.

The bath bead compositions disclosed in our foregoing application are primarily constituted by prilled urea combined with a dye and a minor proportion, generally from 0.1–25%, preferably from 0.5–15%, of the weight of the composition, of at least one active bath composition ingredient such as an emollient, a surfactant, and the like. If desired, fragrances and/or germicides can also be present in the composition. It is also desirable to include, as an optional constituent, an anti-caking agent, such as hydrolyzed protein or water soluble cornstarch.

It has now been found that high quality bath bead compositions based on prilled urea can be produced if the various active bath components are compounded with the urea prills in a certain manner.

SUMMARY OF THE INVENTION

The present invention contemplates a method for producing a bath bead composition utilizing urea prills as carriers for the various other bath composition ingredients. According to the present method, urea prills are admixed with an oily liquid emollient to distribute the emollient substantially uniformly on the prills, and thereafter adhering a powdered surfactant to the emollient-bearing prills to provide non-segregating, substantially free-flowing, surfactant-coated bath beads. To produce dyed bath beads, moisture-containing urea prills are commingled with a water-soluble dye, preferably in dry powder form, to distribute the dye over the external surface of the prills prior to the distribution of the emollient on the prills.

If desired, additional ingredients such as fragrant substances, buffering agents, germicides, preservatives and/or anti-caking agents can also be incorporated into the bath bead composition.

DESCRIPTION OF PREFERRED EMBODIMENTS

The urea beads or prills which constitute the major portion of the bath bead composition are commercially available under the designation "prilled urea." The urea prills are round, relatively hard beads having capacity to absorb or retain a small amount of an oily liquid such as an emollient and/or fragrance that may be utilized in a bath bead composition. The particle size distribution for the prills can vary considerably. Preferably at least about 98 percent of the beads pass through Sieve No. 6 of U.S. Sieve Series and are retained on Sieve No. 20 of U.S. Sieve Series. Thus, the average prill diameter usually is in the range of about 0.13 inch to about 0.035 inch.

The compositions of this invention, when dissolved in water in an amount to provide a urea concentration of approximately 1.0 weight percent, do not significantly modify the pH of normally neutral bath water but give a bath pH in the range of 5–8, preferably 5.5 to 7. If desired, a buffering agent can be included in the composition to further stabilize the pH. The composition is used in the bath in a concentration of 0.05–0.5 weight percent.

The prilled urea constitutes at least 50 weight percent of a bath bead composition. In general, urea does not irritate the skin or mucous membranes and, if ingested, acts as a mild diuretic.

Urea in powder form is not appropriate because, in that physical form, urea is strongly hygroscopic, whereas, the prilled urea has a much smaller surface area per unit weight and is only slightly hydroscopic. For the production of colored bath beads, it is important that the urea prills contain some moisture, particularly on the external surfaces thereof. Enough moisture must be present to solubilize at least some of the powdered water-soluble dye that is commingled with the prills so as to provide dyed prills. Preferably the moisture content of the prills is about 0.02 percent by weight to about 0.1 percent by weight.

Inasmuch as prilled urea does have a limited tendency to absorb moisture, the small amount of water absorbed or adsorbed on the urea beads from ambient atmosphere usually is sufficient to solubilize the amount of powdered water-soluble dye which is combined with the prills to provide a desired coloration for the bath beads and ultimately for the bath water. In such a case the dye can be applied by simply commingling or mixing the urea prills and the water-soluble dye (usually in the form of a dry powder). If the surface moisture content of the urea prills is too low, the prills can be pre-moistened by temporary storage in open containers in a relatively humid atmosphere, or by subjecting the prills to a fine mist or spray of water prior to or during commingling with the dye.

In instances where the moisture content of the urea prills is very low and it is desired to produce colored bath beads, the water-soluble dye can also be dissolved in water and the resulting solution sprayed as a fine mist over a predetermined amount of prills contained in a tumbling barrel, a rotating pan mixer, or the like mixing vessel as the prills are agitated therein. Care should be exercised however, to limit the amount of water that is introduced so as to avoid caking.

Water-soluble dyes suitable for the present purposes are food, drug and cosmetic dyes or drug and cosmetic dyes, these being normally used as color additives in beverages, confections, and/or pharmaceuticals. The dyes can be of any desired color, in finely divided solid or cyrstalline state, and can be selected from nitro, monoazo, diazo, phthalocyanine, quinoline, xanthene, triacrylmethane, indigoid, vegetable dyes, and the like. Blue and green dyes are preferred as being generally more attractive for the present purposes, Illustrative suitable dye is FD&C Blue No. 1, i.e., a color additive which is principally the disodium salt of ethyl{4-{p-[ethyl(m-sulfobenzyl)amino]-α-(o-sulfophenyl)benzylidene}-2,5-cyclohexadien-1-ylidene}(m-sulfobenzyl)ammonium hydroxide inner salt with smaller amounts of the isomeric disodium salts of ethyl{4-{p-[ethyl(p-sulfobenzyl)amino]-α-(o-sulfophenyl)benzylidene}-2,5-cyclohexadien-1-ylidene}(p-sulfobenzyl)ammonium hydroxide inner salt and ethyl{4-{p-[ethyl(o-sulfobenzyl)amino]-α-(o-sulfophenyl)benzylidene}-2,5-cyclohexadien-1-ylidene}(o-sulfobenzyl)ammonium hydroxide inner salt.

The urea prills, whether dyes or undyed, possess a limited capacity to absorb oily liquids, especially emollients and additionally a fragrant substance such as a perfume or a scent. In the present process, an oily liquid, e.g., an emollient, with or without other substances such as fragrances, perfumes, scents, germicides or the like, is added to the urea prills and distributed therelike. If colored bath beads are the desired end product, the dye is distributed on the prills before the oily liquid.

To introduce the emollient, the prills are agitated with the oily liquid emollient to uniformly distribute the oily liquid over the surface of the prills. Agitation is preferably continued to permit the prills to absorb and/or adsorb at least a portion of the oily liquid emollient which is used in an amount of at least 0.2 percent, preferably about 0.5 to about 10 weight percent, based on the weight of the prills. The maximum amount in each case will depend on the nature of the emollient and the absorptive and/or adsorptive capacity of the prill. In any event, the amount of emollient applied to the prills should not exceed the amount which can be absorbed or adsorbed since this causes the prills to remain sticky which prevents the formation of a free flowing powder.

Suitable emollients for the present purposes are the lower alkanol esters of saturated fatty acids such as isopropyl palmitate, isopropyl myristate, methyl laurate, ethyl stearate, and the like. Also suitable are the glycerol esters of saturated fatty acids, e.g., glyceryl monostearate, glyceryl monolaurate, glyceryl tripalmitate, the cholesterol esters of saturated fatty acids, $C_{12-18}$ alcohols, e.g., cetyl alcohol, stearyl alcohol, lauryl alcohol, and adducts of $C_{12-18}$ alcohols with 1 to 4 moles of ethylene oxide, e.g., ethoxylated lauryl alcohol containing about 1 mole of ethylene oxide per mole of lauryl alcohol, oily liquids, e.g., the vegetable oils such as olive oil, cottonseed oil, corn oil, almond oil, peanut oil, and the like, hydrocarbons such as mineral oils, light liquid petrolatum and the like, and similar absorbable substances which soften the skin. These are used as water-free liquids and the term "oily" denotes the presence of a long hydrocarbon chain and the absence of water.

In preparing the bath bead compositions the oily liquid emollient is admixed with the prills to distribute the emollient in contact with a predetermined amount of the prills to form an initially sticky mass or mixture. Urea prills normally have a relatively dull surface which becomes shiny when the oily emollient is distributed thereon, and this shine can be used to measure the uniformity of distribution of the oily liquid. Thus, after addition of the emollient, the combination is mixed or agitated until the prills present a substantially uniform shiny appearance. Preferably, the prill-and-emollient combination is tumbled or otherwise agitated until the emollient is at least partially absorbed or adsorbed and individual emollient-bearing prills begin to move relative to one another or separate from one another.

Non-absorbable emollients, germicides, fragrances, and the like, can be introduced into the bath beads by first encapsulating such substances in a water-soluble sheath or powder, e.g., water-soluble starch or dextrin, and thereafter adhering the encapsulated substances to the emollient-bearing prills while the surface thereof is still somewhat sticky, i.e., before all the liquid emollient has been absorbed within the prills. A suitable commercially available germicide is 2,4,4'-trichloro-2'-hydroxydiphenyl ether. The germicide can be present in an amount of about 0.1 to about 3 percent by weight of the composition.

It is important that the bath beads include a surfactant which is uniformly distributed and which does not segregate on storage. For this purpose, the sticky surfaces of the emollient-bearing prills are coated with a powdered surfactant having a particle size which is substantially less than the size of the urea prills. If a foaming action is desired, a foaming surfactant is utilized for this purpose. The coating operation can be carried out in a tumbling barrel, a rotating pan mixer, an inclined open-ended rotary drum, by passing the prills through a fluidized bed of the surfactant powder, or in any other convenient manner. The powdered surfactant should be added to the emollient-bearing prills after the emollient thereon has been substantially distributed because otherwise the surfactant powder will absorb emollient yielding lumps which interfere with the uniform distribution of emollient and surfactant. If the emollient-bearing prills are agitated without addition of surfactant, the emollient will be taken up by the prills to form a free-flowing powder, and it is now too late to add the powdered surfactant since it will not associate the prills and the mixture segregates on storage.

Continued agitation after addition of the surfactant permits the absorption or adsorption of the oily liquid to continue until a free-flowing particulate mixture is obtained. The finely divided surfactant particles surprisingly remain associated with the urea prills even though there is no longer enough oily liquid on the surface to cause these prills to stick together. The same amount of oily emollient would not serve to associate the surfactant with the prills if the surfactant is added too late as noted previously.

The average particle size of the surfactant particles is preferably up to about ⅓th the average diameter of the urea prills, and is more preferably less than ⅛th its diameter.

The surfactants which may be used may vary considerably, but since a foaming action is preferred so as to provide a bubble bath effect, anionic surfactants are the preferred surfactants, Particularly preferred foaming surfactant is sodium lauryl sulfate powder, in particular sodium lauryl sulfate powder at least about 75% of which passes through Sieve No. 60, U.S. Sieve Series.

Any non-irritating high foaming solid detergent can be used. Particularly suitable are the anionic sulfates and sulfonates. Illustrative of such detergents are magnesium lauryl sulfate powder, alpha-olefin sulfonate flake or powder, nonyl phenyl sulfonate (flake or powder), or mixtures of these materials. If the surfactant is a liquid, the surfactant is converted to a powder form, e.g., encapsulated, before use.

The foaming surfactant can be used in any desired amount, preferably in an amount of about 1% to about 15% of the weight of the composition. If desired, an anti-caking agent or other ingredients can be combined with the powdered surfactant and the emollient-bearing prills coated with the produced combination.

The anti-caking agents which may be used to prevent sticking as a result of water absorption include finely divided modified proteins, water-soluble polysaccharides such as corn-starch and the like, natural gums, and similar substances. Salts which absorb moisture by forming hydrates and which do not induce significant alkalinity in the small proportions utilized can also be used, for example, anhydrous magnesium sulfate. Anti-caking agents are well known, per se, and their use is itself conventional.

To stabilize the pH of the bath water, powdered buffering agents such as citric acid, fumaric acid, tartaric acid, and the like, can also be adhered onto the emollient-bearing prills together with the powdered surfactant. Similarly, powdered preservatives such as the lower alkanol esters of parahydroxybenzoic acid, e.g., methyl paraben, propyl paraben, mixtures thereof, and the like, can be incorporated into the bath bead composition when practicing the present invention.

Either in the presence or absence of the high foaming surfactant, tests indicate that no oily film or ring is left in the bathtub after continued use of the compositions of this invention. These compositions are also not affected by hard water which would usually form scum on or in the bath water.

The following illustrative bath bead compositions can be made by the method of the present invention.

| EMOLLIENT BATH BEAD COMPOSITION | |
|---|---|
| Component | Parts by Weight |
| Prilled urea | 94.3 |
| Oil-soluble, ethoxylated lauryl alcohol[1] | 2.0 |
| Sodium lauryl sulfate powder[2] | 2.5 |
| Fumaric acid (buffering agent) | 0.5 |
| Perfume | 0.5 |
| Mixture (2:1) of methyl paraben and propyl paraben | 0.2 |
| Water-soluble dye (FD&C Blue No. 1) | trace |
| | 100.00 |

[1]contains about 1 mole of ethylene oxide per mole of lauryl alcohol.
[2]about 90 percent passing through Sieve No. 40, U.S. Sieve Series.

| EMOLLIENT BUBBLE BATH COMPOSITION | |
|---|---|
| Component | Parts by Weight |
| Prilled urea | 89.2 |
| Isopropyl palmitate | 2.0 |
| Alpha-olefin ($C_{12-14}$) sulfonate | 8.0 |
| Perfume | 0.8 |
| Water-soluble dye (FD&C Blue No. 1) | trace |
| | 100.00 |

| EMOLLIENT BUBBLE BATH WITH DEODORANT ACTION | |
|---|---|
| Component | Parts by Weight |
| Prilled urea | 89.0 |
| 2,4,4'-trichloro-2'-hydroxy-diphenyl ether (germicide) | 0.2 |
| Isopropyl myristate | 2.0 |
| Alpha-olefin ($_{12-14}$) sulfonate | 8.0 |
| Perfume | 0.8 |
| Water-soluble dye (FD&C Blue No. 1) | trace |
| | 100.00 |

The present method is further illustrated by the following process examples.

EXAMPLE 1

Preparation of Emollient-Bearing, Urea-Based Bath Beads

Prilled urea (about 100 pounds) passing through a No. 6 Sieve and retained on a No. 20 Sieve (U.S. Sieve Series) is introduced into a powder mixer and power to the mixer is turned on so that the urea prills are agitated. Thereafter oil-soluble ethoxylated lauryl alcohol (about 2.25 pounds) is sprayed onto the agitated prills, and the agitation is continued until the urea prills develop a substantially uniformly shiny surface. Thereafter, powdered sodium lauryl sulfate passing through U.S. Sieve Series No. 40 Sieve (about 2.75 pounds) is mixed in with the emollient-bearing prills, and agitation is continued until surfactant-coated, free-flowing prills are produced.

EXAMPLE 2

Preparation of Colored Bath Beads

Urea prills (about 95 pounds) passing through a No. 6 Sieve and retained on a No. 20 Sieve (U.S. Sieve Series) are introduced into a power mixer and agitated. During agitation powdered, water-soluble dye (FD&C Blue No. 1, about 0.1 pound) is added to the power mixer, and the produced admixture is agitated for about 10 minutes until a substantially uniform blue color develops on the prills.

Thereafter, ethoxylated lauryl alcohol (about 2 pounds) and a perfume (about 0.5 pound) are sprayed onto the produced dyed prills until individual prills begin to separate from one another and tumble free of each other. At this time sodium lauryl sulfate powder (about 2.5 pounds; about 90% passing through U.S. Sieve Series No. 40 Sieve) is introduced into the mixer and the formed mixture is agitated until the prills are free-flowing.

EXAMPLE 3

Preparation of Colored, Urea-Based Bath Beads

Urea prills (about 100 pounds) having substantially the same particle size distribution as in Example 2 but a very low moisture content (less than about 0.02 weight percent) are introduced into a power mixer and agitated. Dry, powdered dye (FD&C Blue No. 1) is added to the mixer and the produced mixture is agitated for about 10 minutes. Thereafter, water (about 0.06 pound) is sprayed as a fine mist onto the agitated mixture, and agitation is continued for an additional time period of about 10 minutes to fully develop the color on the prills.

After the prills in the power mixer exhibit a substantially uniform blue color, isopropyl palmitate (about 2.25 pounds) and a perfume (about 1 pound) are sprayed onto the colored prills, and agitation is continued until the prills become shiny. Then a powdered alpha-olefin ($C_{12}$–$C_{14}$) sulfonate (about 8 pounds) is added to the mixer and the mixer contents further agitated until freely flowing, blue-colored prills are produced.

The foregoing discussion and the examples are intended as illustrative and are not to be taken as limiting. Still other process variations are possible without departing from the spirit and scope of the present invention.

The invention is defined in the claims which follow. We claim:

1. A method for producing a non-segregating, free-flowing bath bead composition which comprises admixing urea prills with an oily liquid emollient in an amount of at least about 0.2 to about 10 weight percent, based on the weight of the prills, distributing said emollient substantially uniformly on said prills to provide emollient-bearing prills, adding to said emollient-bearing prills a powdered surfactant in an amount to provide about 1 to about 15 weight percent, based on the weight of the composition, and agitating the mixture of emollient-bearing prills and powdered surfactant while said emollient is absorbed or adsorbed into said prills to produce a free-flowing particulate composition in which the surfactant remains associated with the beads in a non-segregating fashion.

2. The method in accordance with claim 1 wherein the mixture of urea prills with oily liquid emollient is agitated to distribute the emollient substantially uniformly on said prills; and this agitation is continued until individual emollient-bearing prills begin to separate from one another whereupon said powdered surfactant is added to said emollient-bearing prills.

3. The method in accordance with claim 1 wherein the powdered surfactant is a foaming surfactant.

4. The method in accordance with claim 1 wherein a fragrant substance is distributed onto the prills with said oily liquid emollient.

5. The method in accordance with claim 1 wherein a powdered buffering agent is added to the emollient-bearing prills.

6. The method in accordance with claim 1 wherein a powdered preservative is added to the emollient-bearing prills.

7. The method in accordance with claim 1 wherein an anti-caking agent in dry powder form is commingled with the powdered surfactant prior to addition to the surfactant to the emollient-bearing prills.

8. The method in accordance with claim 1 wherein admixing of the urea prills with the liquid emollient is carried out by agitating the prills and spraying the emollient onto the prills while the prills are agitated.

9. The method in accordance with claim 1 wherein said urea prills are dyed with a water-soluble dye prior to the addition of said liquid emollient.

10. The method in accordance with claim 1 wherein the urea prills have an average diameter in the range of about 0.13 inch to about 0.035 inch.

11. The method in accordance with claim 10 wherein said surfactant has an average diameter up to about ¼th the average diameter of said prills.

12. A method of producing a bath bead composition which comprises:
providing urea prills having moisture on the surface thereof in an amount sufficient to solubilize a water-soluble dye;
commingling said prills and a water-soluble dye to distribute said dye over the surface of said prills thereby producing dyed prills;
contacting the dyed prills with an absorbable liquid emollient to provide on the dyed prills at least about 0.2 to about 10 weight percent of the emollient, based on the weight of the prills to provide emollient-bearing prills; and
coating the emollient-bearing prills with a powdered surfactant in an amount to provide about 1 to about 15 weight percent, based on the weight of the composition.

13. The method in accordance with claim 12 wherein the prills have a moisture content of about 0.02 to about 0.1 weight percent, based on the weight of the prills.

14. The method in accordance with claim 12 wherein the dye in dry powder form is distributed substantially uniformly over the entire surface of the prills.

15. The product produced by the method of claim 1.

* * * * *